(12) United States Patent
Divoux

(10) Patent No.: US 8,409,294 B2
(45) Date of Patent: Apr. 2, 2013

(54) CUP COMPONENT OF AN ORTHOPAEDIC JOINT PROSTHESIS

(75) Inventor: Laurent Divoux, Deyvillers (FR)

(73) Assignee: Depuy (Ireland) (IE)

( * ) Notice: Subject to any disclaimer, the term of this patent is extended or adjusted under 35 U.S.C. 154(b) by 63 days.

(21) Appl. No.: 12/933,269

(22) PCT Filed: Feb. 26, 2009

(86) PCT No.: PCT/EP2009/001588
§ 371 (c)(1),
(2), (4) Date: Feb. 9, 2011

(87) PCT Pub. No.: WO2009/115196
PCT Pub. Date: Sep. 24, 2009

(65) Prior Publication Data
US 2011/0130845 A1    Jun. 2, 2011

(30) Foreign Application Priority Data

Mar. 18, 2008    (GB) .................................. 0804998.3

(51) Int. Cl.
*A61F 2/32*    (2006.01)
(52) U.S. Cl. .................................................. 623/22.32
(58) Field of Classification Search ...... 623/22.15–22.4, 623/23.12, 23.43, 19.11–19.14, 20.22, 21.13, 623/23.4, 22.11–22.14; 606/91, 99
See application file for complete search history.

(56) References Cited

U.S. PATENT DOCUMENTS

| | | | |
|---|---|---|---|
| 3,605,123 A | | 9/1971 | Hahn |
| 3,903,549 A | * | 9/1975 | Deyerle ...................... 623/22.36 |
| 4,298,993 A | * | 11/1981 | Kovaleva et al. .......... 623/22.36 |
| 4,792,337 A | * | 12/1988 | Müller ........................ 623/22.36 |
| 4,840,632 A | * | 6/1989 | Kampner .................... 623/22.36 |

(Continued)

FOREIGN PATENT DOCUMENTS

| | | |
|---|---|---|
| EP | 265712 A1 | 5/1988 |
| EP | 1005290 A1 | 6/2000 |

(Continued)

OTHER PUBLICATIONS

PCT International Search Report and Written Opinion PCT/EP2009/001588 dated May 18, 2009.

(Continued)

*Primary Examiner* — Alvin J. Stewart

(57) ABSTRACT

A cup component of an orthopaedic joint prosthesis comprises a hollow shell wherein the head part of a mating component of the joint can be received. The shell has a flange at its open face extending around at least part of its periphery with at least two major threaded bores extending through the flange. The flange also provides at least one minor threaded bore, wherein the diameter of the minor bore is less than that of the major bores and the pitch of the thread in the minor bore is less than that of the thread in the major bores. The cup component includes at least two fixation screws whose shanks have approximately equal diameters, each of which is threaded on its external surface (i) to engage the thread a respective one of the bores in the shell flange, and (ii) to threadingly engage the bone, and a temporary screw having a self-drilling tip for forming a bore in a bone, and a diameter and a thread which are suitable for threadingly engaging the thread in the minor bore.

13 Claims, 4 Drawing Sheets

U.S. PATENT DOCUMENTS

| | | | |
|---|---|---|---|
| 4,961,748 A * | 10/1990 | Frey et al. | 623/22.21 |
| 5,314,488 A * | 5/1994 | Hayashi et al. | 623/22.36 |
| 5,314,490 A * | 5/1994 | Wagner et al. | 623/22.36 |
| 5,425,778 A * | 6/1995 | Zichner et al. | 623/22.29 |
| 5,702,477 A * | 12/1997 | Capello et al. | 623/22.21 |
| 5,871,548 A * | 2/1999 | Sanders et al. | 623/22.36 |
| 5,879,399 A * | 3/1999 | Church | 623/22.25 |
| 5,925,048 A | 7/1999 | Ahmad | |
| 5,931,870 A * | 8/1999 | Cuckler et al. | 623/22.21 |
| 6,162,257 A * | 12/2000 | Gustilo et al. | 623/22.32 |
| 6,340,370 B1 | 1/2002 | Willert et al. | 623/22.38 |
| 6,416,553 B1 * | 7/2002 | White et al. | 623/22.38 |
| 6,440,131 B1 | 8/2002 | Haidukewych | 606/60 |
| 6,458,161 B1 * | 10/2002 | Gibbs et al. | 623/22.32 |
| 6,620,200 B1 * | 9/2003 | Descamps et al. | 623/22.32 |
| 7,291,177 B2 * | 11/2007 | Gibbs | 623/22.25 |
| 7,485,148 B2 * | 2/2009 | Wozencroft et al. | 623/22.36 |
| 7,604,667 B2 * | 10/2009 | DeSmet et al. | 623/22.36 |
| 7,682,399 B2 * | 3/2010 | Shields et al. | 623/22.24 |
| 7,713,306 B2 * | 5/2010 | Gibbs | 623/22.25 |
| 7,722,679 B2 * | 5/2010 | Radzinsky | 623/33 |
| 7,918,896 B2 * | 4/2011 | DeSmet et al. | 623/22.36 |
| 7,947,083 B2 * | 5/2011 | Ashton et al. | 623/22.36 |
| 8,123,814 B2 * | 2/2012 | Meridew et al. | 623/22.28 |
| 8,123,816 B2 * | 2/2012 | Shields et al. | 623/22.35 |
| 2002/0042654 A1 * | 4/2002 | Masini | 623/22.32 |
| 2003/0009234 A1 | 1/2003 | Treacy | |
| 2004/0220674 A1 * | 11/2004 | Pria | 623/19.12 |
| 2005/0288793 A1 * | 12/2005 | Dong et al. | 623/22.28 |
| 2006/0052876 A1 * | 3/2006 | Wozencroft et al. | 623/22.32 |
| 2006/0058887 A1 | 3/2006 | DeSmet | |
| 2006/0149263 A1 | 7/2006 | Newcomb | |
| 2007/0100458 A1 * | 5/2007 | Dalla Pria | 623/19.13 |
| 2007/0162029 A1 | 7/2007 | Whitmore | |
| 2007/0250175 A1 * | 10/2007 | Meridew et al. | 623/22.21 |
| 2008/0172130 A1 * | 7/2008 | Macara | 623/22.21 |
| 2008/0262627 A1 * | 10/2008 | DeSmet et al. | 623/22.36 |
| 2008/0306606 A1 * | 12/2008 | Shields | 623/22.21 |
| 2009/0088865 A1 * | 4/2009 | Brehm | 623/22.21 |
| 2009/0149961 A1 | 6/2009 | Dallmann | 623/22.35 |
| 2009/0281630 A1 * | 11/2009 | Delince et al. | 623/19.13 |
| 2010/0049327 A1 * | 2/2010 | Isch et al. | 623/19.12 |
| 2010/0087927 A1 * | 4/2010 | Roche et al. | 623/19.11 |
| 2010/0217399 A1 * | 8/2010 | Groh | 623/19.11 |
| 2010/0222886 A1 * | 9/2010 | Wiley et al. | 623/19.13 |
| 2011/0144758 A1 * | 6/2011 | Deffenbaugh | 623/19.11 |
| 2012/0016487 A1 * | 1/2012 | Conway et al. | 623/22.38 |
| 2012/0083895 A1 * | 4/2012 | Conway et al. | 623/22.35 |
| 2012/0179270 A1 * | 7/2012 | Nevins et al. | 623/22.35 |
| 2012/0209392 A1 * | 8/2012 | Angibaud et al. | 623/19.11 |
| 2012/0221111 A1 * | 8/2012 | Burkhead et al. | 623/19.11 |
| 2012/0245702 A1 * | 9/2012 | Pappas et al. | 623/22.12 |

FOREIGN PATENT DOCUMENTS

| | | |
|---|---|---|
| EP | 1588677 A2 | 10/2005 |
| EP | 1800626 A2 | 6/2007 |
| GB | 2117646 A | 10/1983 |
| WO | WO 2004069107 A1 | 8/2004 |
| WO | WO 2006031911 A2 | 3/2006 |
| WO | WO 2006112955 A2 | 10/2006 |
| WO | WO 2007118708 A2 | 10/2007 |

OTHER PUBLICATIONS

UK Search Report GB0804998.3 date of search Jun. 18, 2009.

* cited by examiner

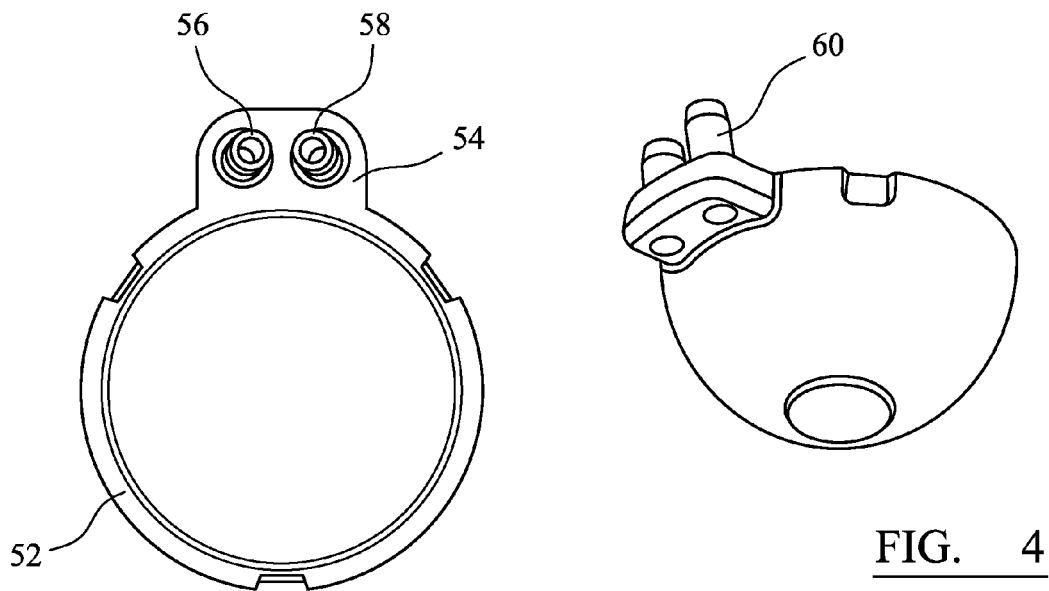
FIG. 3
FIG. 4
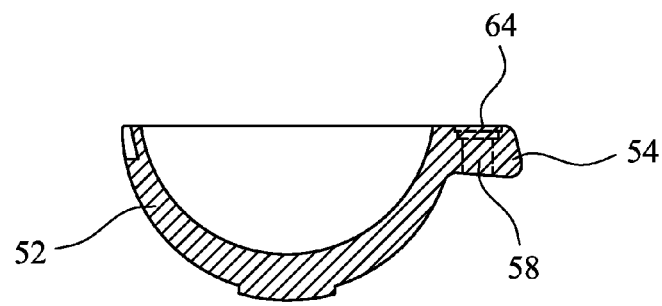
FIG. 5
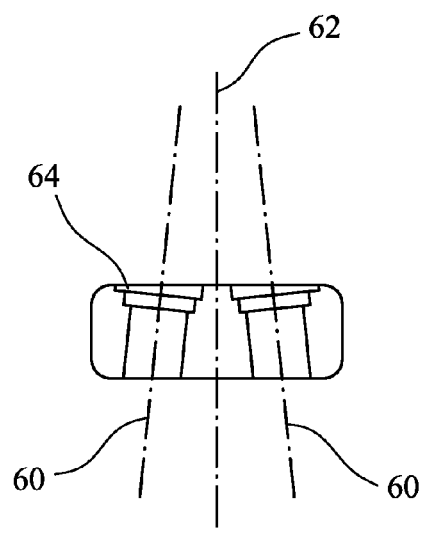
FIG. 6
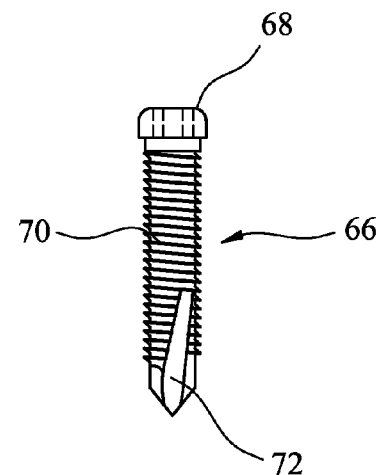
FIG. 7

CUP COMPONENT OF AN ORTHOPAEDIC JOINT PROSTHESIS

CROSS REFERENCE TO RELATED APPLICATION

This application is a National Stage 35 U.S.C. 371 of International Patent Application PCT/EP2009/001588, filed Feb. 26, 2009.

BACKGROUND OF THE INVENTION

This invention relates to a cup component of an orthopaedic joint prosthesis.

Orthopaedic joint prostheses for replacement of joints such as the hip and shoulder joints generally comprise a cup component and a mating component which has a convex head which can be received in the cup and can articulate relative to the cup. For example a hip joint prosthesis can comprise a femoral component having a stem part which can be implanted in the intramedullary canal of the femur and a head part on a neck which is inclined to the axis defined by the intramedullary canal. The joint prosthesis includes an acetabular component which comprises a metal shell which is fixed within the patient's acetabulum and a bearing part, frequently formed from a polymeric material such as ultra-high molecular weight polyethylene, which is fixed within the shell. An anatomic shoulder joint prosthesis can comprise a humeral component having a stem part and a convex head, and a glenoid component with a bearing part which defines a concave bearing surface against which the head of the humeral component can articulate. A reverse shoulder joint prosthesis can comprise a glenoid component with a convex head part, and a humeral component with a stem part and an epiphyseal part which, with a bearing part, defines a concave bearing surface against which the head part of the glenoid component can articulate.

BRIEF SUMMARY OF THE INVENTION

Commonly a cup component (which itself or in conjunction with a bearing part provides a concave surface for articulation with a head part) is fastened to the patient's bone using bone screws which pass through the wall of the cup component into the underlying bone tissue. For example, in the case of an acetabular component of a hip joint prosthesis, the component can have a number of holes provided in it at and generally around the pole. However such fixation techniques cannot be used when the quality or the quantity of the bone tissue underlying the cup component is deficient.

US-A-2006/0058887 discloses an acetabular cup component which has a pair of transversely protruding lugs at its open face. Each of the lugs has a threaded bore extending through it for receiving a screw which can threadingly engage its bore and also the underlying bone tissue, to fix the cup component to the bone.

The present invention provides a technique for implanting the cup component of a joint prosthesis, using at least two fixation screws, and a temporary screw with a self drilling tip by which the cup component can be held in place while holes are prepared in the bone for the fixation screws.

Accordingly in one aspect the invention provides a cup component of an orthopaedic joint prosthesis, which comprises:

a. a hollow shell in which the head part of a mating component of the joint can be received, the shell having a flange at its open face extending around at least part of its periphery with at least two major threaded bores extending through the flange, the flange also providing at least one minor threaded bore, in which the diameter of the minor bore is less than that of the major bores and the pitch of the thread in the minor bore is less than that of the thread in the major bores, b. at least two fixation screws whose shanks have approximately equal diameters, each of which is threaded on its external surface (i) to engage the thread a respective one of the bores in the shell flange, and (ii) to threadingly engage the bone, and c. a temporary screw having a self-drilling tip for forming a bore in a bone, and a diameter and a thread which are suitable for threadingly engaging the thread in the minor bore.

In another aspect, the invention provides a method of implanting the cup component of an orthopaedic joint prosthesis having a hollow shell in which the head part of a mating component of the joint can be received, the shell having a flange at its open face extending around at least part of its periphery with at least first and second threaded bores extending through the flange, in which the method includes the steps of:

a. placing the cup component in a prepared cavity, b. inserting through the first threaded bore a temporary screw having a self-drilling tip for forming a bore in a bone, so that the screw cuts a bore in bone tissue adjacent to the cavity and engages the bone threadingly, and also engages the thread in the first threaded bore, c. using a drill to prepare a bore in the bone which is aligned with the second threaded bore in the flange, d. inserting a fixation screw through the second threaded bore so that it threadingly engages the bore in the bone which is aligned with the second threaded bore.

The technique that is provided by the present invention enables a shell to be located appropriately relative to a patient's bone using an inserter instrument (for example, in the case of an acetabular cup component, as disclosed in WO-A-2004/069107), and held in that location and by means of a temporary screw while a drill is used to prepare bores in the patient's bone to receive fixation screws. The inserter instrument can be removed during the drilling step. Removal of the inserter instrument during the drilling step can facilitate drilling. The temporary screw with its self-drilling tip can be deployed to hold the shell in position without first having to form a bore for the temporary screw using a drill.

The drill can be used to prepare a bore in the bone which is aligned with the first threaded bore in the flange. However, the bore in the bone which is cut by means of the temporary screw can often mean that a separate drilling step need not be performed.

The invention can make use of a drill guide which can be located in a bore in the flange to control the alignment of a drill bit which extends through that bore. This can also help to protect the threads and other features of the bore in the flange when the drill is used to cut a bore in the bone. The drill guide can be placed in a bore in the flange. The drill guide can have a threaded exterior surface so that it engages a thread within the bore. The drill guide can preferably have a bore size which is such that a drill bit is a sliding fit in the guide.

The component can include an adaptor which has a threaded peripheral edge to engage the thread in one of the major bores and a threaded internal bore within it to receive the temporary screw so that the adaptor provides the minor bore when fitted within one of the major bores. The adaptor can be used to adapt one of the major threaded bores so that the temporary screw can be inserted through that bore to form a bore in the bone and to fix the shell to the bone. Threaded engagement between the temporary screw and the thread in bore in the flange (directly or through an adaptor when the bore is one of the major bores) means that the shell can be held stably in the cavity in the bone, with the temporary screw acting effectively as a strut. The use of one of the major threaded bores for the temporary screw has the advantage that the size of the flange can be minimised.

Preferably, the adaptor has a limiter feature on its external surface to limit the extent to which it can be threaded into the major bore. The limiter can be in the form of a discontinuity in the thread on the adaptor or a lug or a flange which extends at least part way around the face which remains exposed when the adaptor is located within its major bore in the cup flange.

Preferably, the adaptor has an engagement feature on the face which remains exposed when the adaptor is located within its major bore to engage an instrument by which the adaptor can be rotated within the said major bore. The engagement feature might be in the form of for example two or more partial slots arranged around the rim of the adaptor which can be engaged by the blade of a tool such as a flat bladed screw driver or a multibladed driver such as a star driver. The bore in which the temporary screw can be received can have a non-circular cross-section at the exposed face of the adaptor, for example hexagonal, for receiving the end of a driver tool.

The flange can have at least two major threaded bores extending through it and in addition at least one minor threaded bore extending through it. The additional minor threaded bore for the temporary screw can be used to fix the shell within a patient's bone cavity while first and second bores are drilled for receiving fixation screws, and while the fixation screws are provided in the first and second bores to fix the shell within the patient's bone cavity. This has the advantage that the shell can be held more securely during the steps of drilling the bone and placing the fixation screws.

Preferably the minor bore can be provided in the flange at a point between the first and second major bores, optionally displaced radially outwardly relative to the major bores.

The flange can extend continuously between the first and second bores. The flange can be discontinuous so that there is a gap between the parts of the flange in which the first and second bores are provided so that, for example the flange effectively comprises a plurality of lugs.

The arrangement of the fixation bores around the periphery of the shell can be designed to suit the requirements of a particular patient. The angle subtended between the bores at the axis of the shell (in the plane of the open face of the shell) will generally be not more than about 40°, preferably not more than about 30°, for example not more than about 20°. The angle will generally be at least about 5°, for example at least about 10°.

The axes of the major bores in the flange can be approximately parallel to the polar axis of the shell. It can be preferred for the axes to be inclined relative to the polar axis of the shell so that the fixation screws can be aligned to engage optimally with the available bone surrounding the cavity. The use of fixation screws at angles which are inclined to the polar axis of an acetabular prosthesis is disclosed in EP-A-1588677.

It can be preferred for at least one of the major threaded bores to have a bushing located within it which can be manipulated within the bore so that the orientation of the axis which is defined by the bushing can be adjusted relative to the axis which is defined by the bore. The thread which is engaged by the fixation screw can be provided by the bushing. Preferably, the bushing can be expanded transversely to engage the internal surface of the bushing to lock the bushing against manipulation within the bore. A bushing of this kind is known for use in other applications, for example as disclosed in EP-A-1005290 in a bone plate for use in spinal applications.

Preferably, the ratio of the diameter (referring to the shank of the screw) of the fixation screw to the diameter of the temporary screw is at least about 1.1, more preferably at least about 1.2. Preferably, the ratio of the diameter of the fixation screw to the diameter of the temporary screw is not more than about 2, more preferably not more than about 1.7.

Preferably, the diameter of the fixation screw is at least about 3 mm, more preferably at least about 4 mm. Preferably, the diameter of the fixation screw is not more than about 7.5 mm, more preferably not more than about 6 mm.

Preferably, the diameter of the temporary screw is at least about 2 mm, more preferably at least about 3 mm. Preferably, the diameter of the temporary screw is not more than about 6 mm, more preferably not more than about 5 mm.

Preferably, the ratio of the pitch of the fixation screw to the pitch of the temporary screw is at least about 1.1, more preferably at least about 1.2. Preferably, the ratio of the pitch of the fixation screw to the pitch of the temporary screw is not more than about 3.0, more preferably not more than about 2.5.

Preferably, the pitch of the fixation screw is at least about 0.7 mm, more preferably at least about 1.0 mm. Preferably, the pitch of the fixation screw is not more than about 2.0 mm, more preferably not more than about 1.5 mm.

Preferably, the pitch of the temporary screw is at least about 0.4 mm, more preferably at least about 0.5 mm. Preferably, the pitch of the temporary screw is not more than about 1.0 mm, more preferably not more than about 0.7 mm.

The shell will frequently be made from a metal. Metallic materials which can be used in the manufacture of orthopaedic joint prostheses are known, and include titanium and its alloys, certain stainless steels, and certain alloys which include cobalt and chromium. The shell might be made from materials other than metals, for example ceramic materials such as an aluminium oxide or a zirconium oxide.

The external surface of the shell can be provided with a coating which promotes ingrowth of bone tissue. For example, the external surface of the shell can have a porous structure, for example as in components which are sold by DePuy Orthopaedics Inc under the trade mark POROCOAT. A technique for manufacturing such components is disclosed in U.S. Pat. No. 3,605,123. The external surface can be provided with a coating of a material that promotes bone ingrowth, such as a hydroxyapatite material.

The shell can be configured for fixation in a prepared cavity in a patient's bone using a bone cement material. The features of a shell component which make it appropriate for fixation using a bone cement material are known.

The shell can be configured to receive a bearing component which has a bearing surface for articulation with the head of the other component of the joint. The head can be the natural head of the patient's bone (for example the head of the humerus in the case of a shoulder joint). Frequently however the head will be the head of the mating component of the joint prosthesis. The bearing component can be made from a material which has good bearing properties. Examples of suitable materials for the bearing component include polymers such as ultrahigh molecular weight polyethylene. Techniques for fixing a bearing component to an orthopaedic joint prosthesis shell component are known, for example using matching tapered surfaces, or spring clips in aligned grooves etc.

The temporary screw should preferably be capable of penetrating bone and forming a threaded engagement with the bone without the need first to prepare the bone by forming a pilot bore within the bone (at least to the full length that is necessary to accommodate the screw). Screws which can drill a bore in a bone and cut a thread in the bone are known, for example from U.S. Pat. No. 5,925,048, US-A-2006/0149263 and US-A-2007/0162029.

The thread on the fixation screws or on the temporary screw might be provided in two portions, with a first portion closer to the tip of the screw to engage the bone and a second portion closer to the head of the screw to engage the thread in the flange of the shell. Preferably, the diameter of the first portion of the screw is smaller than the diameter of the second portion of the screw, so that the first portion can pass through the bore in the flange of the shell without engaging the threads within the bore. The pitch of the first portion of the screw will generally be approximately the same as the pitch of the second portion of the screw. In this way, the shell will not be made to move as the screw is advanced through the bone and through the bore in the flange.

The material of the screws should be selected for compatibility with the material of other components of the joint prosthesis with which they will come into contact, directly or indirectly (for example through the action of body fluids) when in use. The screws should be capable of withstanding the forces which are applied to them in use, during temporary fixation in the case of the fixation screw, and after implantation in the case of the fixation screws. The screws will usually be made from a metallic material. Materials which are commonly used in the manufacture of bone screws are known, and include for example titanium and its alloys, certain stainless steels, and certain alloys which include cobalt and chromium.

BRIEF DESCRIPTION OF THE DRAWINGS

Embodiments of the invention will now be described by way of example with reference to the accompanying drawings, in which:

FIG. 3 is a view from above of a first embodiment of an acetabular component of a hip joint prosthesis, with a guide sleeve located in each of the fixation holes in its flange.

FIG. 4 is a perspective view from below of the acetabular component shown in FIG. 3.

FIG. 5 is a sectional elevation through the acetabular component shown in FIG. 3.

FIG. 6 is a cross-section through the flange of the acetabular component shown in FIG. 3, on the line IV-IV.

FIG. 7 is a side view of a fixation screw which can be used with the acetabular component shown in FIG. 3.

DETAILED DESCRIPTION OF THE INVENTION

Figure 1:
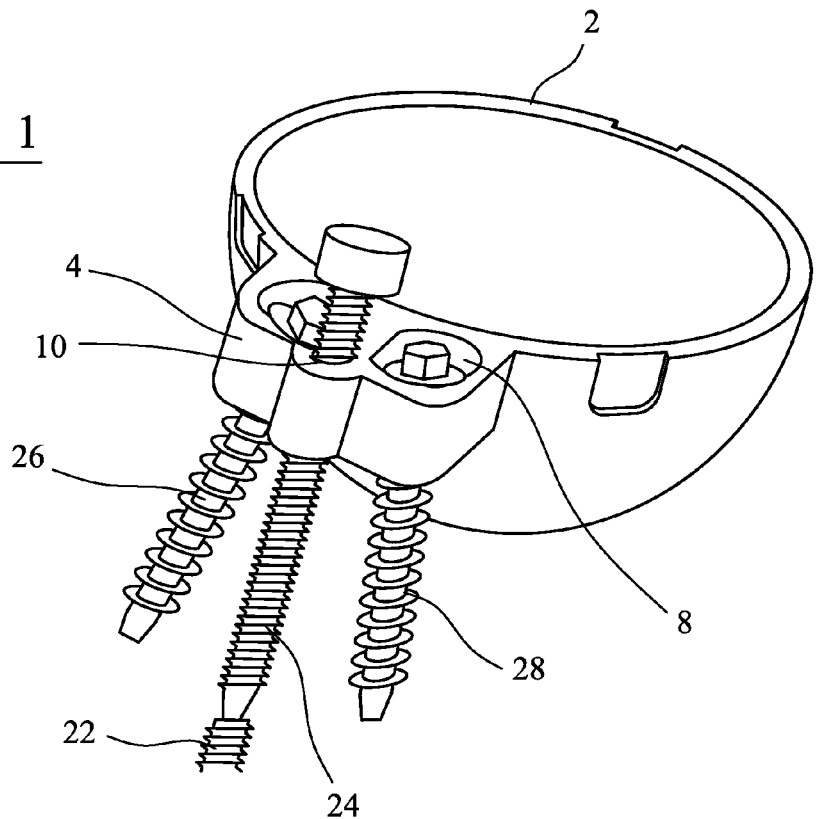
FIG. 1 is an isometric view of an acetabular component of a hip joint prosthesis, with temporary and fixation screws located in respective bores in the flange of a shell.
Figure 2:
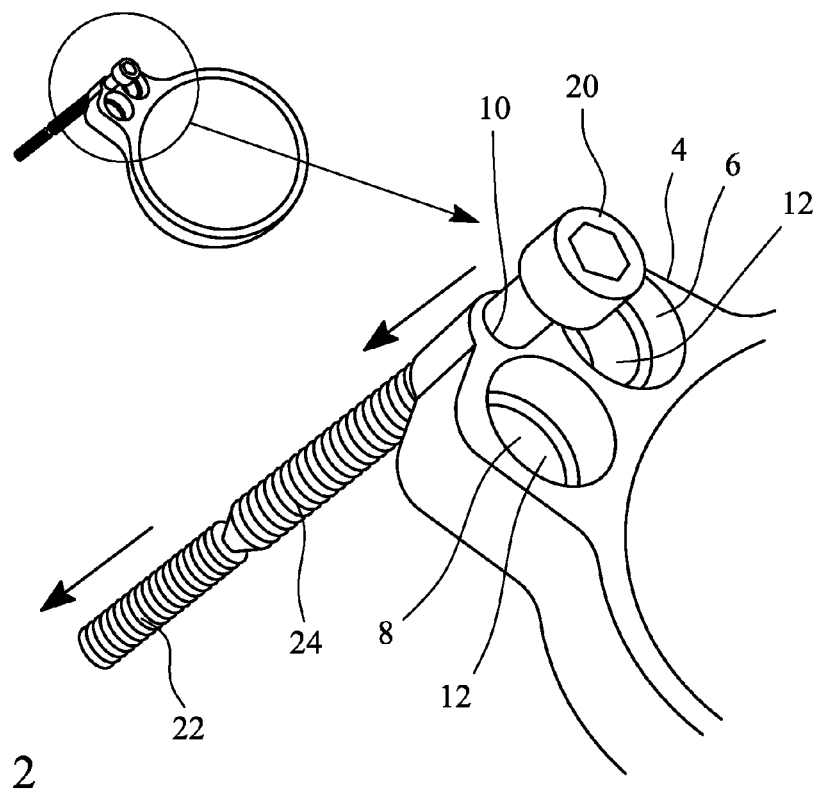
FIG. 2 is an enlarged view of the flange on the shell of the component shown in FIG. 1.

Referring to the drawings, FIGS. 1 and 2 show the shell 2 of an acetabular cup component of a hip joint prosthesis. The shell has an outwardly extending flange 4 at its open face. The flange has three bores formed in it. First and second bores 6, 8 have a larger diameter than a third bore 10. The third bore is located between the first and second bores, displaced outwardly from the first and second bores.

As shown in FIG. 2, each of the first and second bores 6, 8 has a bearing surface 12 which is defined by part of a sphere. The first and second bores can receive bushings which have an external surface which is defined by part of a sphere. The bushings can be articulated within their respective bores by virtue of the mating spherical surfaces on the bushings and the bores. These features are also incorporated in the embodiment which is shown in FIGS. 8 to 12 and are described below in relation to that embodiment.

The bushings have a threaded bore which extends through them which can be aligned with the respective bore in the flange 4 when the bushings are located in the bores. Each of the bushings is split so that it can be expanded by means of an outwardly flared portion on a screw which is inserted in the bushing. The bushings therefore provide threads in the first and second bores in the flange of the shell.

The cup component includes a temporary screw 20. The temporary screw has a threaded distal portion 22 and a threaded proximal portion 24. The diameter of the shank of the to distal portion is 2.4 mm. The diameter of the shank of the proximal portion is 3.1 mm.

The pitch of the threads on the proximal and distal portions is 0.5 mm. The thread on the distal portion of the temporary screw is configured so that it cuts a thread in bone tissue. The thread on the proximal portion of the temporary screw is configured so that it can engage the thread in the third bore 10.

The distal end of the temporary screw is configured so that it can drill a bore in a bone. For example, it can have the bore cutting features which are disclosed in U.S. Pat. No. 5,925,048.

The cup includes first and second fixation screws 26, 28. Each of these screws has a thread which extends from the distal tip to close to the head. The thread is configured so that it can cut a thread in bone into which it is screwed. The threads are also configured to engage the threads in the bushings in the first and second bores 6, 8. Each of the fixation screws has an outwardly flared portion at its head which, when screwed into the bushing, causes the bushing to expand radially outwardly so that it is gripped against internal surfaces of the bores against articulation.

Implantation of the cup component shown in FIGS. 1 and 2 involves the following steps:
1. Prepare the acetabulum to receive the shell 2.
2. Locate the shell in the prepared acetabulum using a shell manipulator, for example as disclosed in WO-A-2004/069107.
3. Pass the distal 22 portion of the temporary screw 20 through the third bore 10 in the flange 4 of the shell until the tip of the screw engages the surface of the patient's bone or the proximal portion 24 of the screw engages the thread in the third bore.
4. Turn the temporary screw to cause it to drill a bore in the bone and to cause the thread on the distal portion to cut a thread in the bore in the bone and so to threadingly engage the bone, and also to cause the thread on the proximal portion of the screw to engage the thread in the third bore in the flange of the shell, until the shell is held rigidly relative to the patient's bone.
5. Remove the shell manipulator.
6. Use a power drill to cut bores in the bone to receive first and second fixation screws, the bores in the bone being aligned with the first and second bores in the flange.
7. Insert the first and second fixation screws 26, 28 into the first and second bores in the flange of the shell.
8. Turn the screws so that they engage the threads in the bushings within the bores and pass through the bores, and then pass into the bores which have been drilled in the bone.
9. Continue to turn the first and second fixation screws to cause them to cut threads in the bores in the bone until the heads of the screws become seated in the bushings, so as to cause the bushings to expand outwardly so that they are gripped by the mating surfaces of the bores in the flange.
10. Optionally, remove and discard the temporary screw.

FIGS. 3 to 5 show the shell 52 of an acetabular component of a hip joint prosthesis. The shell has an outwardly extending flange 54 at its open face. The flange has two bores 56, 58 formed in it. As shown in more detail in FIG. 6, the axes 60 of the bores are arranged so that they are not parallel to a line 62 which is perpendicular to the flange. Each of the bores has an enlarged socket 64 at one end.

Each of the bores is threaded internally. As shown in FIGS. 3 and 4, each of the bores has within it a guide sleeve 60. The guide sleeves are described in more detail below with reference to FIGS. 14 and 15. Each of the guide sleeves has a threaded external surface, in which the thread on the guide sleeves can engage the threads. A guide sleeve can be threaded internally so that it can be engaged by the thread on a temporary screw. A guide sleeve can be used to guide the cutting bit on a drill in a step which involves preparing the bone to receive a fixation screw.

FIG. 7 shows a fixation screw 66 which comprises a head 68 which is a snug fit in the socket 64 in the flange, and a threaded shank 70. The screw can be threadingly received in one of the bores 56, 58 in the flange 54 on the shell, and can be threadingly engaged with a prepared bore in a bone to fix the acetabular component in place. The screw has bore cutting flutes 72 at its distal tip.

Figure 8:
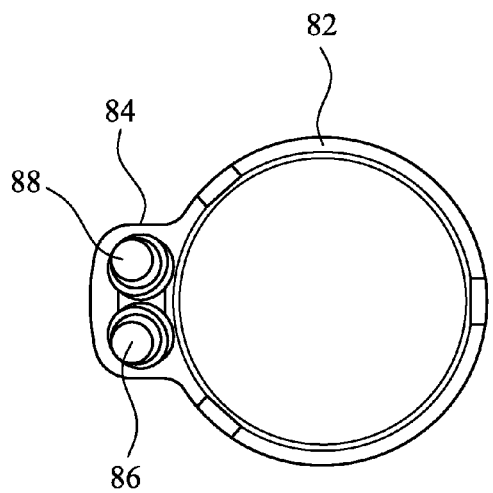
FIG. 8 is a view from above of a first embodiment of an acetabular component of a hip joint prosthesis.
Figure 9:
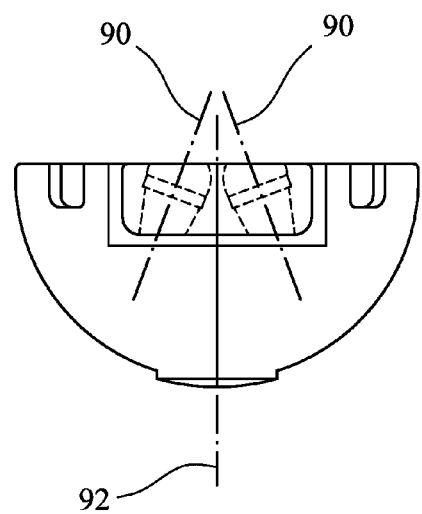
FIG. 9 is a view from one side of the acetabular component shown in FIG. 8.
Figure 10:
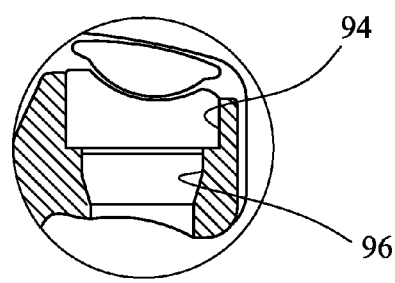
FIG. 10 is an cross-section through the flange of the acetabular component shown in FIG. 8, on the line VIII-VIII.

FIGS. 8 to 10 show the shell 82 of an acetabular component of a hip joint prosthesis. The shell has an outwardly extending flange 84 at its open face. The flange has two bores 86, 88 formed in it. The axes 90 of the bores are arranged so that they are not parallel to a line 92 which is perpendicular to the flange. Each of the bores 86, 88 has a threaded portion 94 which can receive the threaded portion of a guide sleeve (not shown) in the same way as is shown in FIGS. 3 and 4. The guide sleeve is described in more detail below with reference to FIGS. 14 and 15.

Each of the bores 86, 88 has a bearing surface 96 which is defined by part of a sphere.

Figure 11:
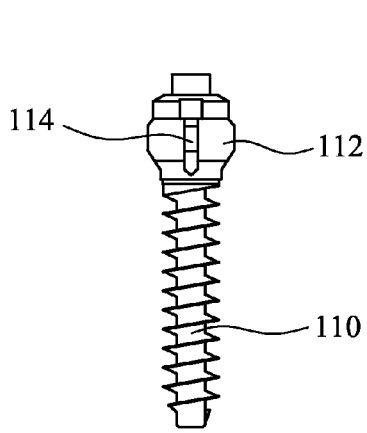
FIG. 11 is a view from one side of a fixation screw which can be used with the acetabular component shown in FIG. 8.
Figure 12:
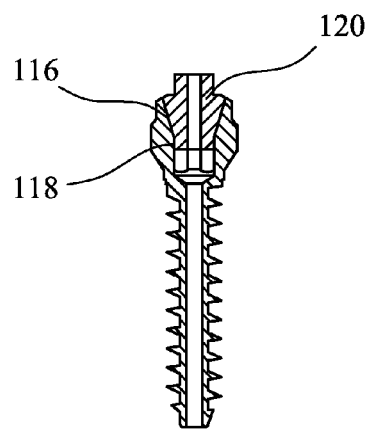
FIG. 12 is a sectional elevation through the fixation screw shown in FIG. 10.

The shell 82 which is shown in FIGS. 8 to 10 can be used with a polyaxial screw of the kind which is shown in FIGS. 11 and 12. The polyaxial screw has a threaded shank 110, in which the thread is suitably configured so that it can cut into and engage with bone.

The head of the screw has a portion 112 with a rounded external surface, whose shape approximates to part of a sphere. The rounded portion of the head of the screw has a plurality of splits, of which one 114 is visible in FIG. 11. The head of the screw has a bore extending into it which has an inwardly tapered initial portion 116 and a threaded distal portion 118. The bore contains an expander screw 120 which is threaded towards its tip. The thread on the expander screw is configured to engage the thread in the distal portion of the bore.

The polyaxial screw can be located in either of the bores 86, 88 in the flange 84 on the shell so that the shank 110 extends through the bore and the rounded portion 112 of the head sits in the bearing surface 96 of the bore. The orientation of the shank of the screw relative to the axis of the bore can be adjusted to suit the requirements of a particular implantation. The orientation can be locked by screwing the expander screw 120 into the head of the polyaxial screw, so that the action of the tapered portion 116 of the expander screw against the bore in the polyaxial screw causes the rounded portion of the head of the polyaxial screw to expand.

Figure 13:
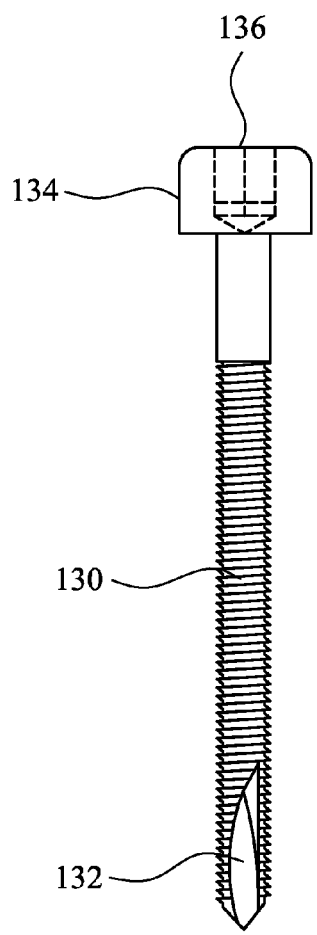
FIG. 13 is a side view of a temporary screw which can be used in the system of the invention.

FIG. 13 shows a temporary screw which can be used in the system of the present invention. It comprises a threaded shank 130 which has flutes 132 at its tip which can drill a hole in a bone when the screw is screwed into a bone. The thread on the shank is shaped so that it can cut a thread into the bone as the screw is screwed into the bone.

The head 134 of the screw has a hexagonal socket 136 formed in it for receiving the hexagonal tip of a driving instrument.

Figure 14:
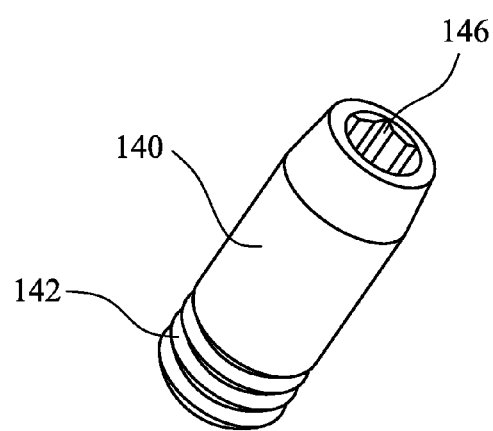
FIG. 14 is a perspective view of a guide sleeve which can be fitted into a bore in the flange on an acetabular component.
Figure 15:
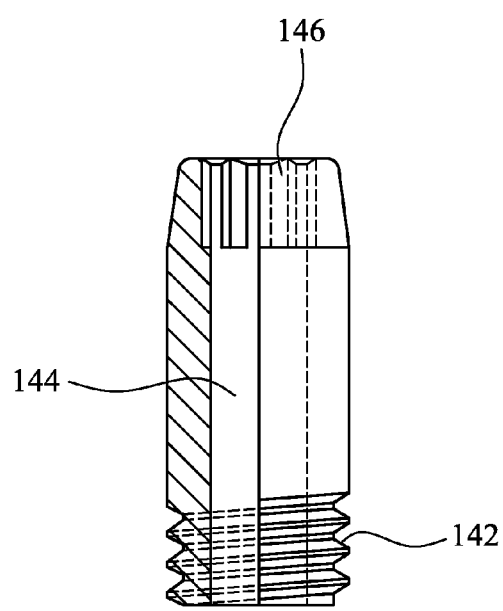
FIG. 15 is a side view, partially in section, of the guide sleeve shown in FIG. 14.

FIGS. 14 and 15 show a guide sleeve which can be fitted into a bore in the flange on an acetabular component. The guide sleeve comprises a generally cylindrical body 140 which has a thread 142 on its outer surface which can be received in one of the bores in the flange on a shell. The guide sleeve has a bore 144 extending through it. The bore has a hexagonal socket portion 146 at the end which is opposite to the threaded end, for receiving the hexagonal tip of a driving instrument.

The bore can have a threaded internal surface when the guide sleeve is intended to receive a temporary screw.

The bore can have a plain internal surface when it is not required to be engaged threadingly by a screw, when it can be used to guide a drill bit.

The invention claimed is:

1. A cup component of an orthopaedic joint prosthesis for fixing to a patient's bone, which comprises:
    a hollow shell configured to receive a head part of a mating component of the joint prosthesis, the shell having a periphery, an open face and a flange proximate the open face extending around at least part of the periphery, the flange having at least two major threaded bores extending therethrough and at least one minor threaded bore extending therethrough, wherein the diameter of the minor bore is less than the diameter of the at least two major bores and the pitch of the thread in the minor bore is less than that of the thread in the at least two major bores,
    at least two fixation screws, each of which comprise a shank having an external surface, the shanks having approximately equal diameters, each of which is threaded on the external surface and is configured (i) to engage the thread of a respective one of the bores in the shell flange, and (ii) to threadingly engage the bone, and
    a temporary screw having a self-drilling tip for forming a bore in the bone, and a diameter and a thread that are configured to threadingly engage the thread in the minor bore.

2. The cup component of claim 1, further comprising an adaptor that has a threaded peripheral edge sized and configured to engage the thread in one of the at least two major bores and a threaded internal bore therein to receive the temporary screw so that the adaptor provides the minor bore when fitted within one of the major bores.

3. The cup component of claim 2, wherein the adaptor has an external surface and a limiter feature thereon to limit the extent to which the adaptor can be threaded into the major bore.

4. The cup component of claim 2, wherein the adaptor has an engagement feature on the face that remains exposed when the adaptor is located within one of the at least two major bores to permit an instrument to engage the engagement feature and rotate the adaptor within the major bore.

5. The cup component of claim 1, wherein the flange has at least two major threaded bores extending therethrough and in addition at least one minor threaded bore extending therethrough.

6. The cup component of claim 1, wherein at least one of the major threaded bores has a bushing located therein that can be manipulated within the bore so that the orientation of the axis defined by the bushing can be adjusted relative to the axis defined by the bore, and wherein the thread which is engaged by the fixation screw is provided by the bushing, and wherein the bushing is expandable transversely to engage the internal surface of the bushing to lock the bushing against manipulation within the bore.

7. The cup component of claim 1, wherein the ratio of the diameter of the shank of the fixation screw to the diameter of the shank of the temporary screw is at least about 1.5.

8. The cup component of claim 1, wherein the ratio of the diameter of the shank of the fixation screw to the diameter of the shank of the temporary screw is not more than about 2.0.

9. The cup component of claim 1, wherein the ratio of the pitch of the fixation screw to the pitch of the temporary screw is at least about 1.5.

10. The cup component of claim 1, wherein the ratio of the pitch of the fixation screw to the pitch of the temporary screw is not more than about 2.0.

11. A method of implanting the cup component of an orthopaedic joint prosthesis having a hollow shell wherein the head part of a mating component of the joint can be received, the shell having a periphery, an open face and a flange at the open face extending around at least part of the periphery, the flange having at least a first, a second and a third threaded bore extending therethrough, wherein the method includes the steps of:
  placing the cup component in a prepared cavity;
  inserting through the first threaded bore a temporary screw having a self-drilling tip for forming a bore in a bone, so that the screw cuts a bore in bone tissue adjacent to the cavity and engages the bone threadingly, and also engages the thread in the first threaded bore;
  using a drill to prepare at least two bores in the bone, one each of the two bores being aligned with the second and third threaded bores of the flange;
  inserting a first fixation screw through the second threaded bore so that the first fixation screw threadingly engages the bore in the bone aligned with the second threaded bore;
  inserting a second fixation screw through the third threaded bore so that the second fixation screw threadingly engages the bore in the bone aligned with the third threaded bore; and
  removing the temporary screw.

12. The method of claim 11, further comprising the step of removing the temporary screw before drilling the second of the two bores in the bone.

13. The method of claim 11, wherein the second threaded bore contains an adaptor that has a threaded peripheral edge to engage the thread in the second threaded bore and a threaded internal bore therein to receive the temporary screw, and wherein the method further comprises the step of removing the adaptor.

* * * * *